US00PP34155P2

(12) United States Plant Patent
Bernuetz

(10) Patent No.: US PP34,155 P2
(45) Date of Patent: Apr. 19, 2022

(54) ***ARGYRANTHEMUM* PLANT NAMED 'BONMAD 1651'**

(50) Latin Name: ***Argyranthemum* X *hybrida***
Varietal Denomination: Bonmad 1651

(71) Applicant: Andrew Bernuetz, Silverdale (AU)

(72) Inventor: Andrew Bernuetz, Silverdale (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 17/488,716

(22) Filed: Sep. 29, 2021

(51) Int. Cl.
*A01H 5/02* (2018.01)
*A01H 6/14* (2018.01)

(52) U.S. Cl.
USPC ..... Plt./406
CPC ..... *A01H 6/14* (2018.05)

(58) Field of Classification Search
USPC ..... Plt./406
CPC ..... A01H 6/14; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Argyranthemum* plant named 'Bonmad 1651', characterized by its upright, uniform and mounded plant habit; vigorous growth habit; early and freely flowering habit; single-type inflorescences with ray florets that are reddish purple in color and disc florets that are initially dark red in color becoming orange in color with development; and good garden performance.

1 Drawing Sheet

Figure 1:
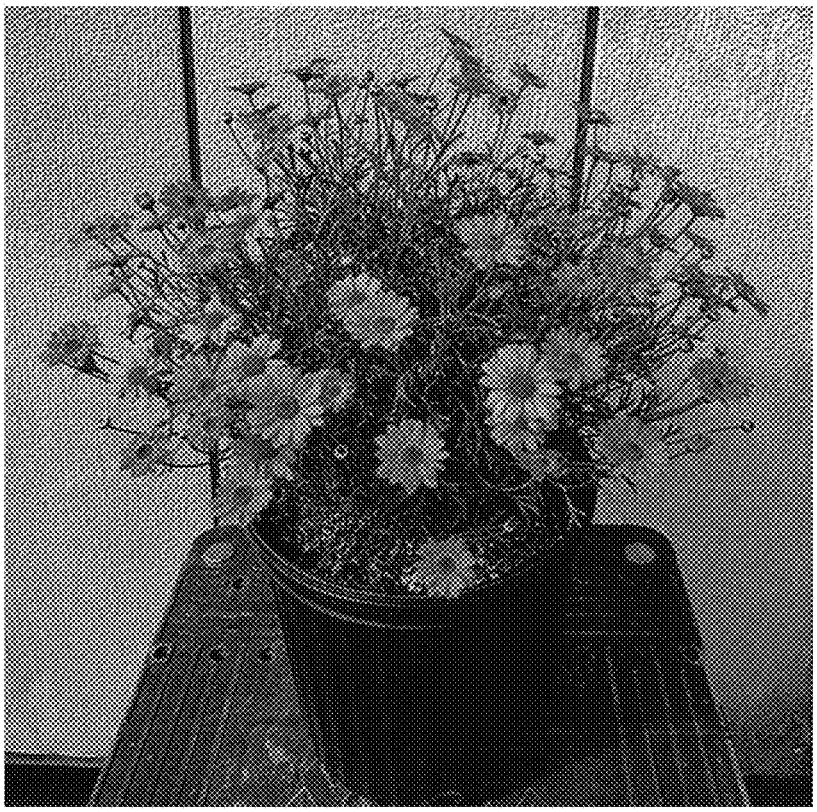

Botanical Designation: *Argyranthemum* X *hybrida*.
Cultivar denomination: 'BONMAD 1651'.

BACKGROUND OF THE INVENTION

The present invention relates to a new and distinct cultivar of *Argyranthemum* plant, botanically known as *Argyranthemum* X *hybrida* and hereinafter referred to by the name 'Bonmad 1651'.

The objective of the breeding program is to create new compact, early and freely flowering *Argyranthemum* plants with attractive floret colors and good garden performance.

The new *Argyranthemum* plant originated from a cross-pollination made by the Inventor in September, 2015 in Yellow Rock, New South Wales, Australia of a proprietary selection of *Argyranthemum* X *hybrida* identified as code number 14-41, not patented, as the female, or seed, parent with a proprietary selection of *Argyranthemum* X *hybrida* identified as code number 11-393, not patented, as the male, or pollen, parent. The new *Argyranthemum* was discovered and selected by the Inventor as a single flowering plant within the progeny of the stated cross-pollination in a controlled environment in Yellow Rock, New South Wales, Australia in February, 2016.

Asexual reproduction of the new *Argyranthemum* plant by vegetative tip cuttings was first conducted in Yellow Rock, New South Wales, Australia in February, 2016. Asexual reproduction by cuttings has shown that the unique features of this new *Argyranthemum* plant are stable and reproduced true to type in successive generations.

SUMMARY OF THE INVENTION

Plants of the new *Argyranthemum* have not been observed under all possible combinations of environmental conditions and cultural practices. The phenotype may vary somewhat with variations in environment such as temperature and light intensity, without, however, any variance in genotype.

The following traits have been repeatedly observed and are determined to be the unique characteristics of 'Bonmad 1651'. These characteristics in combination distinguish 'Bonmad 1651' as a new and distinct *Argyranthemum* cultivar:

1. Upright, uniform and mounded plant habit.
2. Vigorous growth habit.
3. Early and freely flowering habit.
4. Single-type inflorescences with ray florets that are reddish purple in color and disc florets that are initially dark red in color becoming orange in color with development.
5. Good garden performance.

Plants of the new *Argyranthemum* differ primarily from plants of the female parent selection in inflorescence form. Plants of the new *Argyranthemum* have single-type inflorescences whereas plants of the female parent selection have anemone-type inflorescences. In addition, ray florets of plants of the new *Argyranthemum* are reddish purple in color whereas ray florets of plants of the female parent selection are red in color.

Plants of the new *Argyranthemum* differ primarily from plants of the male parent selection in flowering habit as plants of the new *Argyranthemum* are more freely flowering than plants of the male parent selection.

Plants of the new *Argyranthemum* can be compared to plants of the *Argyranthemum* X *hybrida* 'Bonmadrosepi', disclosed in U.S. Plant Pat. No. 22,049. In side-by-side comparisons, plants of the new *Argyranthemum* differ from plants of 'Bonmadrosepi' in the following characteristics:

1. Plants of the new *Argyranthemum* are taller and broader than plants of 'Bonmadrosepi'.
2. Inflorescences of plants of the new *Argyranthemum* have more ray and disc florets than inflorescences of plants of 'Bonmadrosepi'.

3. Ray florets of plants of the new *Argyranthemum* are lighter reddish purple in color than ray florets of plants of 'Bonmadrosepi'.

BRIEF DESCRIPTION OF THE PHOTOGRAPHS

The accompanying photographs illustrate the overall appearance of the new *Argyranthemum* plant. These photographs show the colors as true as it is reasonably possible to obtain in colored reproductions of this type. Colors in the photographs may differ slightly from the color values cited in the detailed botanical description which accurately describe the colors of the new *Argyranthemum* plant.

The photograph at the top of the sheet (FIG. 1) is a side perspective view of a typical flowering plant of 'Bonmad 1651' grown in a container.

Figure 2:
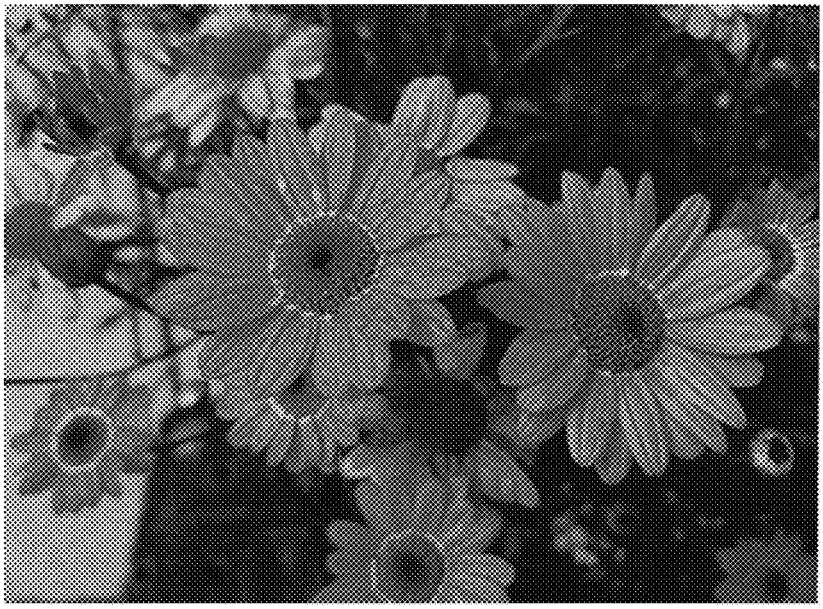

The photograph at the bottom of the sheet (FIG. 2) is a close view of a typical flowering plant of 'Bonmad 1651'.

DETAILED BOTANICAL DESCRIPTION

The aforementioned photographs and following observations and measurements describe plants grown in 24-cm containers during the spring in Higashiomi, Shiga, Japan in an outdoor nursery and under conditions and practices which approximate those generally used in commercial potted *Argyranthemum* production. During the production of the plants, day temperatures averaged 23° C. and night temperatures averaged 13° C. Plants used in the photographs were four months old and plants used for the detailed description were five months old. In the following description, color references are made to The Royal Horticultural Society Colour Chart, 2001 Edition, except where general terms of ordinary dictionary significance are used.

Botanical classification: *Argyranthemum* X *hybrida* 'Bonmad 1651'.

Parentage:

*Female, or seed, parent*.—Proprietary selection of *Argyranthemum* X *hybrida* identified as code number 14-41, not patented.

*Male, or pollen, parent*.—Proprietary selection of *Argyranthemum* X *hybrida* identified as code number 11-393, not patented.

Propagation:

*Type*.—By vegetative terminal cuttings.

*Time to initiate roots, summer*.—About seven days at temperatures of about 18° C. to 21° C.

*Time to initiate roots, winter*.—About ten days at temperatures of about 18° C. to 21° C.

*Time to produce a rooted young plant, summer*.—About three weeks at temperatures of about 18° C. to 21° C.

*Time to produce a rooted young plant, winter*.—About four weeks at temperatures of about 18° C. to 21° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous single-type potted *Argyranthemum*; upright, uniform and mounded plant habit; strong and freely branching growth habit with about five primary lateral branches developing per plant; dense and full plants; pinching will enhance lateral branching; vigorous growth habit.

*Plant height*.—About 33 cm.

*Plant diameter*.—About 42 cm.

*Lateral branches*.—Length: About 17.4 cm. Diameter: About 1.8 mm. Internode length: About 2.3 cm. Strength: Strong; young stems, flexible. Aspect: Upright to somewhat outwardly. Texture: Smooth, glabrous. Color: Close to 138A faintly overlain with close to 178A.

Leaf description:

*Arrangement*.—Alternate, simple.

*Length*.—About 5.2 cm.

*Width*.—About 3.2 cm.

*Lateral lobe length*.—About 1.9 cm.

*Lateral lobe width*.—About 7 mm.

*Depth of lateral lobe incision*.—About 2 cm.

*Shape*.—Obovate, palmately-parted.

*Apex*.—Acute.

*Base*.—Cuneate.

*Margin*.—Palmately-parted.

*Texture, upper and lower surfaces*.—Smooth, glabrous.

*Venation*.—Pinnate, reticulate.

*Color*.—Developing leaves, upper surface: Close to 137A. Developing leaves, lower surface: Close to 137C. Fully expanded leaves, upper surface: Close to 137A; venation, close to 137C. Fully expanded leaves, lower surface: Close to 137B; venation, close to 137C.

*Petioles*.—Length: About 1.5 cm. Diameter: About 3.5 mm. Texture, upper and lower surfaces: Smooth, glabrous. Color, upper surface: Close to 137A. Color, lower surface: Close to 137B.

Inflorescence description:

*Appearance*.—Single-type inflorescence form with oblong to elliptic-shaped ray florets and tubular disc florets; solitary upright inflorescences borne on terminals above foliar plane; ray and disc florets arranged acropetally on a capitulum.

*Fragrance*.—None detected.

*Flowering season and response*.—Plants flower from spring through late autumn in Japan; flowering continuous during this period; early flowering habit, plants begin flowering about eight weeks after sticking unrooted cuttings.

*Inflorescence longevity*.—Inflorescences last about two weeks on the plant; inflorescences persistent.

*Quantity of inflorescences*.—Freely flowering habit with numerous inflorescences developing per lateral branch.

*Inflorescence buds*.—Height: About 8.4 mm. Diameter: About 7.5 mm. Shape: Globose. Color: Close to 71B.

*Inflorescence size*.—Diameter: About 3.5 cm. Depth (height): About 1.2 cm. Diameter of disc: About 1.1 cm. Receptacle diameter: About 9.6 mm. Receptacle height: About 5.3 mm. Receptacle color: Close to 142B.

*Ray florets*.—Quantity and arrangement: About 21 ray florets arranged in one to two whorls; ray florets imbricate. Length: About 1.4 cm. Width: About 6 mm. Shape: Oblong to elliptic. Apex: Rounded or emarginate. Base: Attenuate. Margin: Entire. Texture, upper and lower surfaces: Smooth, glabrous; longitudinally ribbed. Color: When opening, upper surface: Close to NN78A. When opening, lower surface: Close to NN78B. Fully opened, upper surface: Close to 72C; vention, close to 72C; color becoming closer to N74D with subsequent development. Fully opened, lower surface: Close to 72D; venation, close to 72D; color becoming closer to N74D with subsequent development.

*Disc florets*.—Quantity and arrangement: About 183 massed at center of receptacle in numerous whorls. Shape: Tubular. Apex: Acute, five-pointed. Length: About 2.2 mm. Diameter: About 1 mm. Texture: Smooth, glabrous. Color, immature: Close to 59A. Color, mature: Close to 34A and 9B.

*Phyllaries*.—Quantity and arrangement: About 25 arranged in several whorls; phyllaries imbricate. Involucral diameter: About 1.2 cm. Length: About 3.6 mm. Width: About 4.2 mm. Shape: Lanceolate. Apex: Acute. Base: Truncate, fused. Margin: Entire. Texture, upper and lower surfaces: Smooth, glabrous; papery. Color, upper surface: Close to 138A. Color, lower surface: Close to 137A.

*Peduncles*.—Length: About 7.3 cm. Diameter: About 1.4 cm. Aspect: Upright to outwardly. Strength: Strong, flexible. Texture: Smooth, glabrous. Color: Close to 137C.

*Reproductive organs*.—Androecium: Present on disc florets only. Quantity per floret: About five. Filament length: About 1 mm. Filament color: Close to NN155A. Anther shape: Cylindrical. Anther length: About 1.2 mm. Anther color: Close to 21B. Pollen amount: None observed. Gynoecium: Present on both ray and disc florets. Quantity per floret: One. Pistil length: About 4 mm. Stigma shape: Bi-parted. Stigma color: Close to 15B and 59C. Style color: Close to 150C. Ovary color: Close to 145C.

*Seeds and fruits*.—To date, seed and fruit production have not been observed on plants of the new *Argyranthemum*.

Pathogen & pest resistance: To date, resistance to pathogens and pests common to *Argyranthemums* has not been observed on plants grown under commercial conditions.

Garden performance: Plants of the new *Argyranthemum* have been observed to have good garden performance and to tolerate wind, rain and temperatures from about 0° C. to about 35° C.

It is claimed:

1. A new and distinct *Argyranthemum* plant named 'Bonmad 1651' as illustrated and described.

* * * * *